US006463934B1

(12) United States Patent
Johnson, Jr., deceased et al.

(10) Patent No.: US 6,463,934 B1
(45) Date of Patent: Oct. 15, 2002

(54) METHOD FOR PROVIDING ENHANCED BLOOD CIRCULATION

(75) Inventors: Glenn W. Johnson, Jr., deceased, late of Summit, NJ (US), by Glenn W. Johnson, III, legal representative; Daniel A. Berish, Montville, NJ (US); Henry J. McVicker, Naples, FL (US); Anthony Victor Seaber, Jonesboro, NC (US)

(73) Assignee: Aircast, Inc., Summit, NJ (US)

( * ) Notice: Subject to any disclaimer, the term of this patent is extended or adjusted under 35 U.S.C. 154(b) by 0 days.

(21) Appl. No.: 09/592,229

(22) Filed: Jun. 12, 2000

(51) Int. Cl.[7] .................................. A61B 19/00
(52) U.S. Cl. .................................. 128/898; 601/150
(58) Field of Search .................................. 128/898; 601/149, 601/150, 151, 152

(56) References Cited

U.S. PATENT DOCUMENTS 5,496,262 A 3/1996 Johnson, Jr. et al.
5,588,955 A 12/1996 Johnson, Jr. et al.
6,129,688 A * 10/2000 Arkans .................. 601/152
6,231,532 B1 * 5/2001 Watson et al. .............. 601/150

OTHER PUBLICATIONS

Nicolaides et al., "Intermittent sequential pneumatic compression of the legs in the prevention of venous statis and postoperative deep venous thrombosis," published in *Surgery*, vol. 87, No. 1, pp. 69–76, Jan., 1980.

Salzman et al., "Effect of Optimization of Hemodynamics on Fibrinolytic Activity and Antithrombotic Efficacy of External Pneumatic Calf Compression," published in *Ann. Surg.*, vol. 206, No. 5, Nov. 1987, pp. 636–641.

Clagett et al., "Prevention of Venous Thromboembolism," *Chest*, vol. 108, No. 4, Oct. 1995 Supplement, pp. 312S–334S.

Westrich et al., "Prophylaxis against Deep Venous Thrombosis after Total Knee Arthroplasty," *The Journal of Bone and Joint Surgery*, vol. 78–A, No. 6, Jun. 1996.

Heit, J.A., "Current recommendations for prevention of deep venous thrombosis," *Handbook of Venous Disorders*, ch. 17, 1996.

Gardner et al., "The Return of Blood to the Heart," second ed., Chapter 3, pp. 28–59.

Liu et al., "The Effect of Intermittent Pneumatic Compression on Microcirculation of Distant Skeletal Muscle," presented at the 43rd Annual Meeting, Orthopaedic Research Society, Feb. 9–13, 1997, San Francisco, California.

(List continued on next page.)

*Primary Examiner*—Corrine McDermott
*Assistant Examiner*—Tyom Barrett
(74) *Attorney, Agent, or Firm*—Jones, Day, Reavis & Pogue

(57) ABSTRACT

A method of providing enhanced circulation, venous return and microcirculation is achieved by use of intermittent pneumatic compression in alternating periods of application and recovery.

9 Claims, 6 Drawing Sheets

OTHER PUBLICATIONS

Liu et al., "Nitric Oxide: A Possible Regulator of Vasodilation in Distant Skeletal Muscle Induced by Intermittent Pneumatic Compression," presented at the 44th Annual Meeting, Orthopaedic Research Society, Mar. 16–19, 1998, New Orleans, LA.

Comerota et al., "Why Does Prophylaxis With External Pneumatic Compression for Deep Vein Thrombosis Fail?" *The American Journal of Surgery*, vol. 164, Sep. 1992, pp. 265–268.

Liu et al., "Influences of Inflation Rate and Duration on Vasodilatory Effect by Intermittent Pneumatic Compression in Distant Skeletal Muscle," *Journal of Othopaedic Research*. vol. 17, No. 3, pp. 415–420.

Baez, S., "An Open Cremaster Muscle Preparation for the Study of Blood Vessels by in Vivo Microscopy," *Microvascular Research* 5, pp. 384–394 (1973).

Baez, S. et al., "Microvascular Hypersensitivity Subsequent to Chemical Denervation," *Circulation Research*, vol. XX, Mar. 1967, pp. 328–337.

Grant, R.T., "Direct Observation of Skeletal Muscle Blood Vessels (Rat Cremaster)," *J. Physiol.*, (1964), 172, pp. 123–137.

Liu, K. et al., "Intermittent Pneumatic Compression of Legs Increases Microcirculation in Distant Skeletal Muscle," *J. Orthop. Res.*, vol. 17, No. 1, 1999, pp. 88–95.

Anderson et al., "Vascular Isolation of the Rat Cremaster Muscle," *Microvascular Research* 36, pp. 56–63 (1988).

Coe, N.P. et al., "Prevention of deep vein thrombosis in urological patients: A controlled, randomized trial of low-dose heparin and external pneumatic compression boots," *Surgery* (1978), pp. 230–234.

* cited by examiner

METHOD FOR PROVIDING ENHANCED BLOOD CIRCULATION

FIELD OF THE INVENTION

This invention relates to a method for providing enhanced blood circulation. More particularly this invention relates to a method for providing enhanced blood circulation, including circulation, microcirculation, and venous return by the application of intermittent pneumatic compression (IPC) in selected pre-determined time cycles.

BACKGROUND OF THE INVENTION

Intermittent pneumatic compression is the technique of cyclically compressing a limb with air pressure to enhance the circulation of blood. Pressure is applied from a source of compressed air by a control mechanism that intermittently inflates a cuff enveloping all or part of an arm or leg. Parameters that can be controlled in known IPC techniques include the rate of pressurization, the pressure achieved, the rate of depressurization, and the rest duration between pulses. As disclosed in U.S. Pat. No. 5,496,262, assigned to the common assignee and incorporated herein by reference, IPC can also be applied by means of cuffs having more than one chamber, the chambers being disposed at relatively distal and proximal locations along the limb. Additional parameters that can be controlled with multiple-chambered cuffs include the level of pressure that can be provided to each chamber (i.e., graduated compression), and the timing of the application of pressure to each chamber (i.e., sequential compression).

IPC is known to be of therapeutic benefit for a variety of circulatory disorders. For example, the use of IPC is known in the prevention and treatment of edema. IPC is also known as a means for reducing the risk of deep vein thrombosis (DVT). U.S. Pat. No. 5,588,955, also assigned to the common assignee and incorporated herein by reference, discloses a method and apparatus for applying graduated and/or sequential IPC to a limb to prevent DVT. Applicant's assignee also manufactures and sells devices under the trademarks VENAFLOW® and ARTERIOFLOW™ which are used to apply IPC to a patient in need of such therapy.

As disclosed in the aforementioned U.S. Pat. Nos. 5,496,262 and 5,588,955, in IPC as used in the prior art the period of compression is typically short, about ten seconds, and the recovery period between pulses is about a minute, to allow the veins to refill after being emptied by the short pulse of compression. The optimal amount of compression known in prior art devices is in the range of 35–45 mmHg. Further, it is known that the velocity of venous flow during the period of compression is generally proportional to the rate of pressurization. For example, a pulse that reaches maximum pressure in six seconds will have a much greater effect on venous velocity than a pulse that reaches the same maximum pressure in 30 seconds.

Prior researchers studying the effects of IPC on DVT prophylaxis have recommended continuous application of IPC. Nicolaides et al., in "Intermittent sequential pneumatic compression of the legs in the prevention of venous stasis and postoperative deep venous thrombosis," published in *Surgery,* vol. 87, No. 1, pages 69–76, January, 1980, at p. 75 suggested that IPC that was started from the induction of anesthesia and continued until 16–24 hours after an operation was effective in preventing DVT during the time it was applied; and further that a sequential compression device might be even more effective if used for several days during the postoperative period, if not continuously, at least intermittently. In a study by Salzman et al., "Effect of Optimization of Hemodynamics on Fibrinolytic Activity and Antithrombotic Efficacy of External Pneumatic Calf Compression," published in *Ann. Surg*., vol. 206, no. 5 November 1987, pp. 636–641, patients undergoing surgery were treated with IPC as prophylaxis for DVT until they became ambulatory, roughly 3 weeks. Clagett, et al., in "Prevention of Venous Thromboembolism," *Chest,* vol. 108, no. 5 October 1995 Supplement, pp.3125–3345, suggest at p. 3185 that IPC devices must be applied either intraoperatively or as soon as is feasible post-operatively and worn continuously except during ambulation. At page 3195 it is suggested that DVT prophylaxis be provided for at least 7 to 10 days post-operatively. In "Prophylaxis against Deep Vein Thrombosis after Total Knee Arthroplasty," by Westrich, et al., *J. Bone and Joint Surgery*, vol. 78-A, no. 6 June 1996, a device for providing pulsatile pneumatic plantar compression was found to be effective for preventing DVT if applied post-operatively for 96 hours for a mean of 19.2 hours per day. The *Handbook of Venous Disorders,* 1996, in Ch. 17, "Current recommendations for prevention of deep vein thrombosis," by Heit, states at p. 296 "IPC should be initiated preoperatively and continued until the patient is fully ambulatory. The utility of IPC is limited by patient intolerance and noncompliance, non-use during periods of physical therapy, and unsuitability for continued home use after hospital discharge."

In addition to the known effect of DVT prophylaxis, it recently has been learned that IPC also can have an effect on microcirculation in skeletal muscle distant from the site of direct IPC application. Microcirculation is discussed in the text *The Return of Blood to the Heart*, A. M. N. Gardner and R. H. Fox, second ed., Chapter 3, "Microcirculatory Blood flow." A mechanism for this effect is proposed by Liu, et al., in "The Effect of Intermittent Pneumatic Compression of Microcirculation of Distant Skeletal Muscle," presented at the 43rd Annual Meeting, Orthopaedic Research Society, Feb. 9–13, 1997, San Francisco, Calif., which suggests that IPC creates shear stress on the vessel wall which may induce release of nitric oxide (NO) from vascular endothelial cells, producing systemic dilatation of vessels. This hypothesis was supported in Liu, et al., "Nitric oxide: A Possible Regulator of Vasodilation in Distant Skeletal Muscle Induced by Intermittent Pneumatic Compression," presented at the 44th Annual Meeting, Orthopaedic Research Society, Mar. 16–19, 1998, New Orleans, La., wherein the relationship between the IPC-induced vasodilatory effect in distal skeletal muscle and increasing NO release during compression was confirmed by studies using different dosages of N-monomethyl-L-arginine (L-NMMA), an NO synthase inhibitor.

It has been found, however, that the effect of IPC on microcirculation is not constant over the entire time during which IPC is applied. Thus, the effect of IPC measured as vasodilation, i.e., the increase in vessel diameter, has been found to peak after about 20–40 minutes of continuous IPC application, and to decrease thereafter, even while the application of IPC continues. It would be desirable to be able to continue vasodilation over a longer period of time than is currently possible with known IPC techniques.

It is thus one object of the invention to provide enhanced circulation, venous return, and microcirculation over a longer period of time than has been obtained by currently known IPC techniques.

SUMMARY OF THE INVENTION

In accordance with the invention, blood circulation, including circulation, microcirculation, and venous return, is enhanced by the application of IPC in a pre-determined pattern of periods of IPC applications alternating with recovery periods in which lesser or no IPC is applied. It has been found that, surprisingly, the use of a recovery period after a period of IPC application results in greater enhanced circulation subsequent IPC applications, over that which would have been observed in the absence of any recovery period. Use of the inventive method can also enhance microcirculation in skeletal muscle distant from the actual site of IPC application.

DETAILED DESCRIPTION OF THE INVENTION

In this patent, the term "microcirculation" shall mean circulation in the smaller blood vessels of the body, as generally described in Gardner & Fox, *The Return of Blood to the Heart,* 2nd ed., Ch. 3, "Microculatory Blood Flow."

In the practice of the method of the instant invention, IPC is applied to a region of the body for a pre-determined time period, followed by a recovery period during which little or no IPC is applied, after which IPC is applied again. The use of a recovery period between the periods of IPC application is believed to result in greater enhancement of circulation, venous return, and microcirculation, than that observed with the prior art method of continuous IPC without a recovery period in which the IPC effect is known to diminish overtime.

Different cyclic patterns of alternating IPC application periods and recovery periods can be employed as may be desirable in different circumstances. For example, cyclic patterns in accordance with the method of the instant invention can include 60 minutes of IPC operation followed by ten minutes of recovery, followed by 60 minutes of IPC operation (a "60-10-60" cycle); 60 minutes of IPC operation following by five minutes of recovery, followed by 60 minutes of IPC operation (a "60-5-60" cycle); forty minutes of IPC operation followed by either 5 or 10 minutes of recovery, followed by 40 minutes of operation (a "40-5-40" cycle and a "40-10-40" cycle); and alternating periods of 20 minutes of IPC followed by 60 minutes of recovery (a "20-60-20-60" cycle).

The following examples demonstrate the efficacy of the inventive method in enhancing microcirculation in a skeletal muscle distant from the site of IPC application.

EXAMPLE 1

Two groups of rats were subjected to IPC applied to a hind leg in accordance with the method of the instant invention. During the periods of IPC application, the applied pressure was about 35–45 mmHg, full pressurization was reached in less than about one second and maintained for about five seconds, and about 4–5 pulses were applied per minute. In the first group, the cycle of IPC was 40 minutes of IPC application, followed by 5 minutes of recovery, followed by 40 minutes of IPC application (a 40-5-40 cycle). The cycle applied to the second group was 40 minutes of IPC application followed by 10 minutes of recovery, followed by 40 minutes of IPC application (a 40-10-40 cycle). During the recovery periods, no IPC was applied. After the IPC application cycle was complete, the vasodilation of vessels in the rat cremaster muscle was measured by videomicroscopy and the percent change values were averaged within each group.

Figure 1:
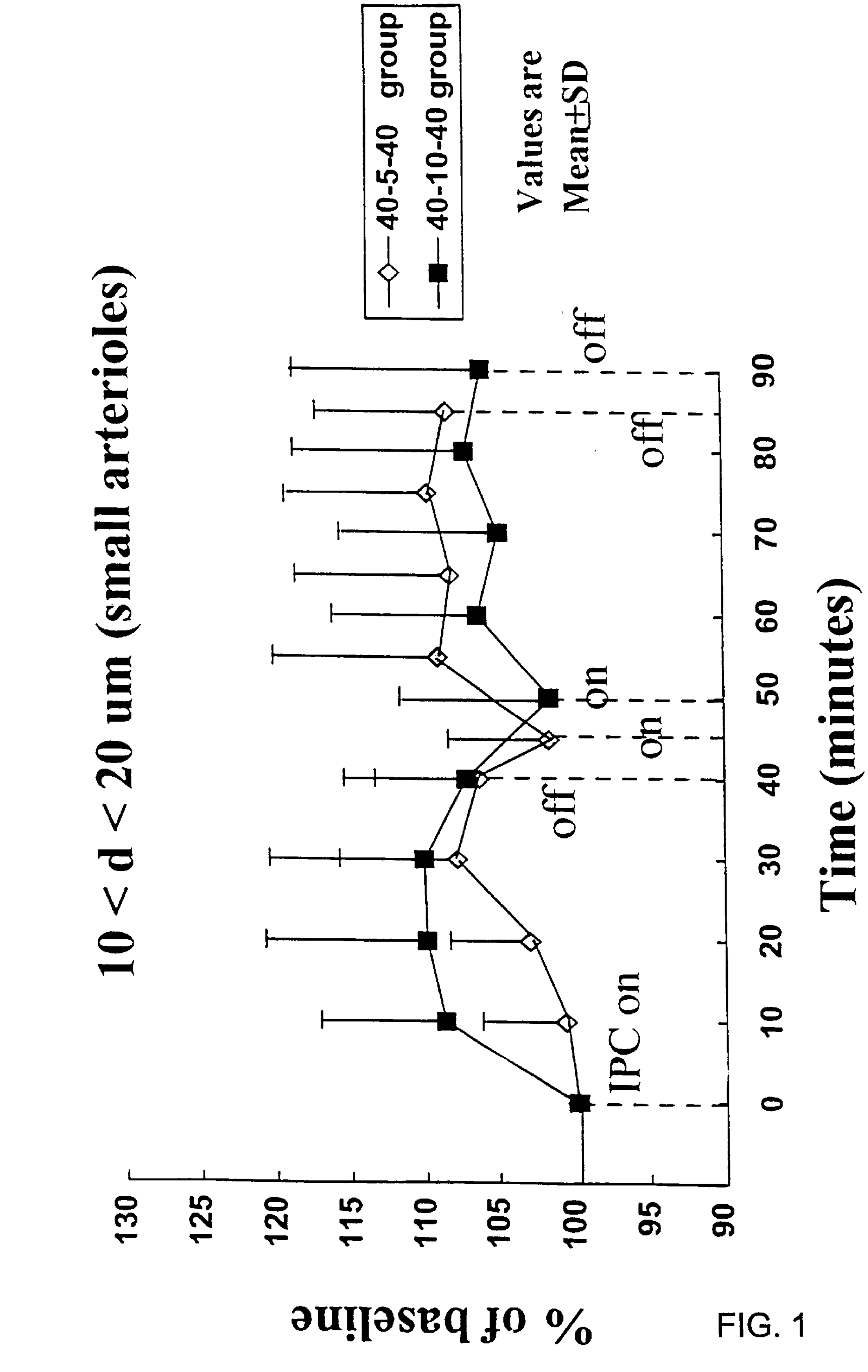
FIG. 1 is a graph showing vasodilation of small arterioles in the cremaster muscle of two groups of rats, the first group subjected to an IPC application cycle of 40-5-40, and the second group subjected to an IPC application cycle of 40-10-40.

FIG. 1 illustrates the vasodilation in small arterioles (10 microns<d<20 microns) of the two groups of rats. The group with the shorter (five minute) recovery showed larger vasodilation in the small arterioles in the second IPC period.

Figure 2:
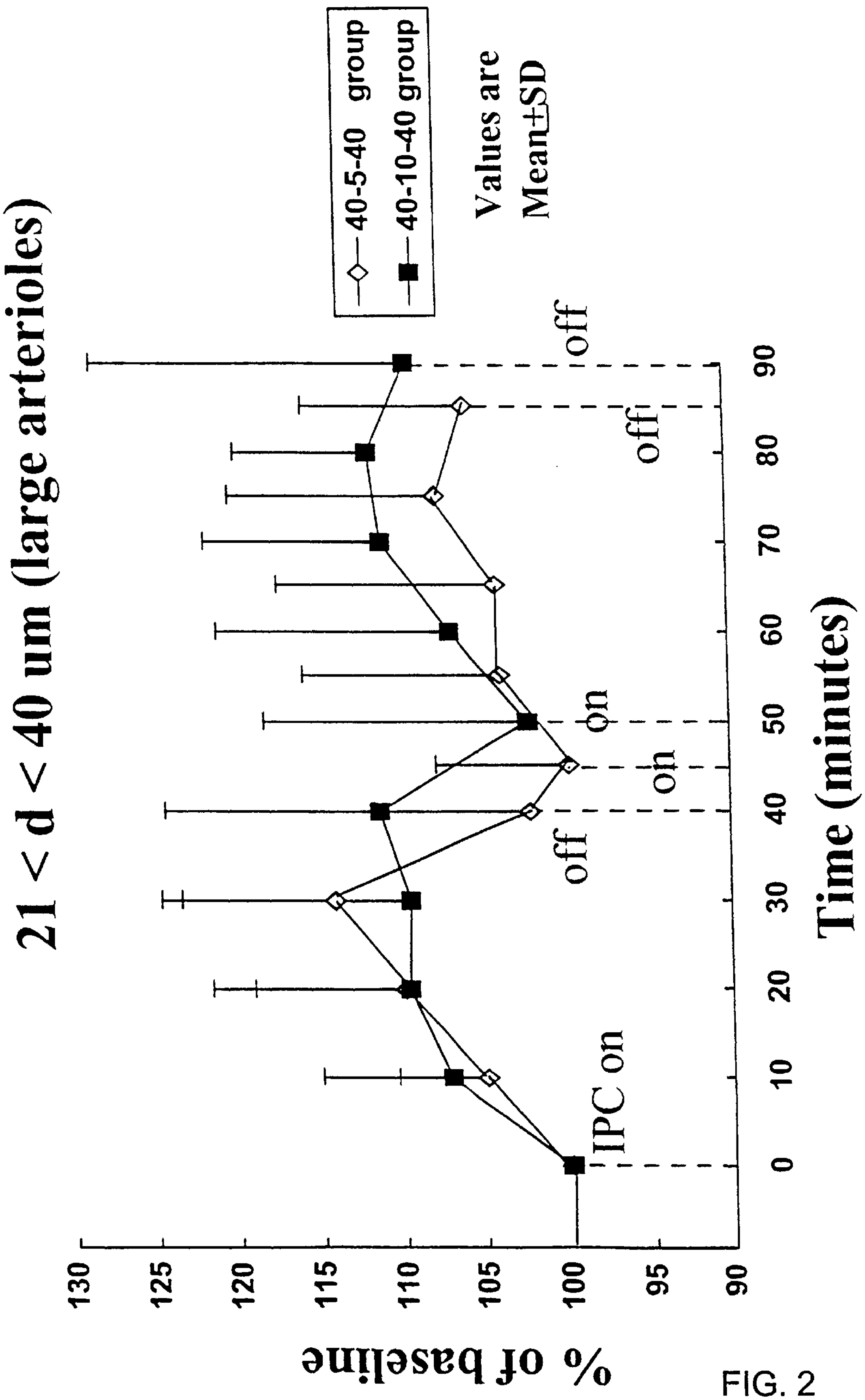
FIG. 2 is a graph showing vasodilation of large arterioles in the cremaster muscle of the same two groups of rats as were tested in FIG. 1.

FIG. 2 illustrates the vasodilation in the large arteriole (21 microns<d<40 microns) for the same two groups of rats. For the larger arterioles, greater vasodilation was observed in the group with the longer (ten minute) recovery period.

Figure 3:
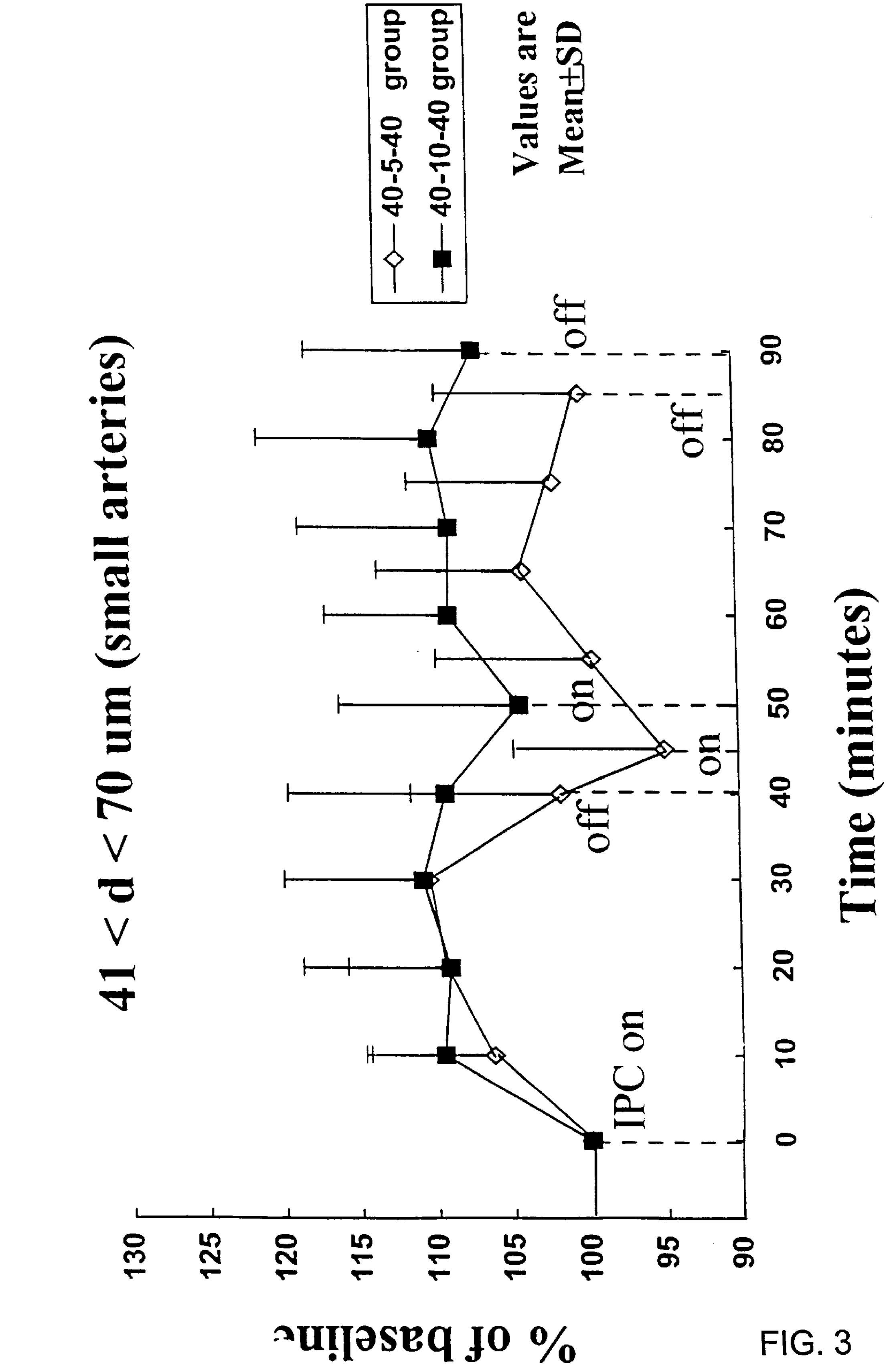
FIG. 3 is a graph showing vasodilation of the small arteries in the cremaster muscle of the same two groups of rats as were tested in FIGS. 1 and 2.

FIG. 3 illustrates the vasodilation in the small arteries (41 microns<d<70 microns) for the same two groups of rats. For the small arteries, greater vasodilation was observed in the group with the longer (ten minute) recovery period.

EXAMPLE 2

Figure 4:
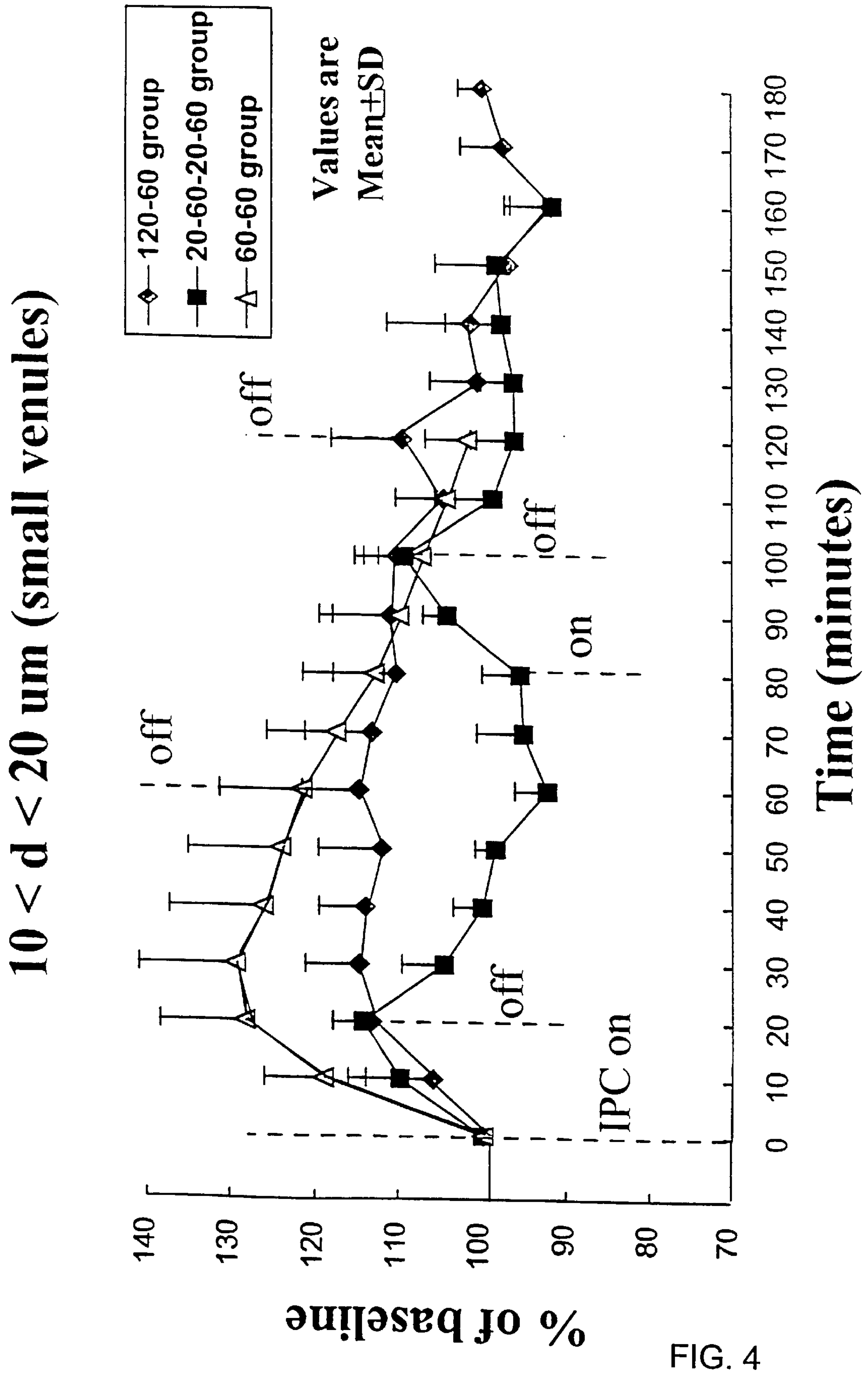
FIG. 4 is a graph showing vasodilation of small venules in the cremaster muscle of three groups of rats, the first group subjected to an IPC application cycle of 120-60; the second group subjected an IPC application cycle of 20-60-20-60; and the third group subjected to an IPC application cycle of 60-60.
Figure 5:
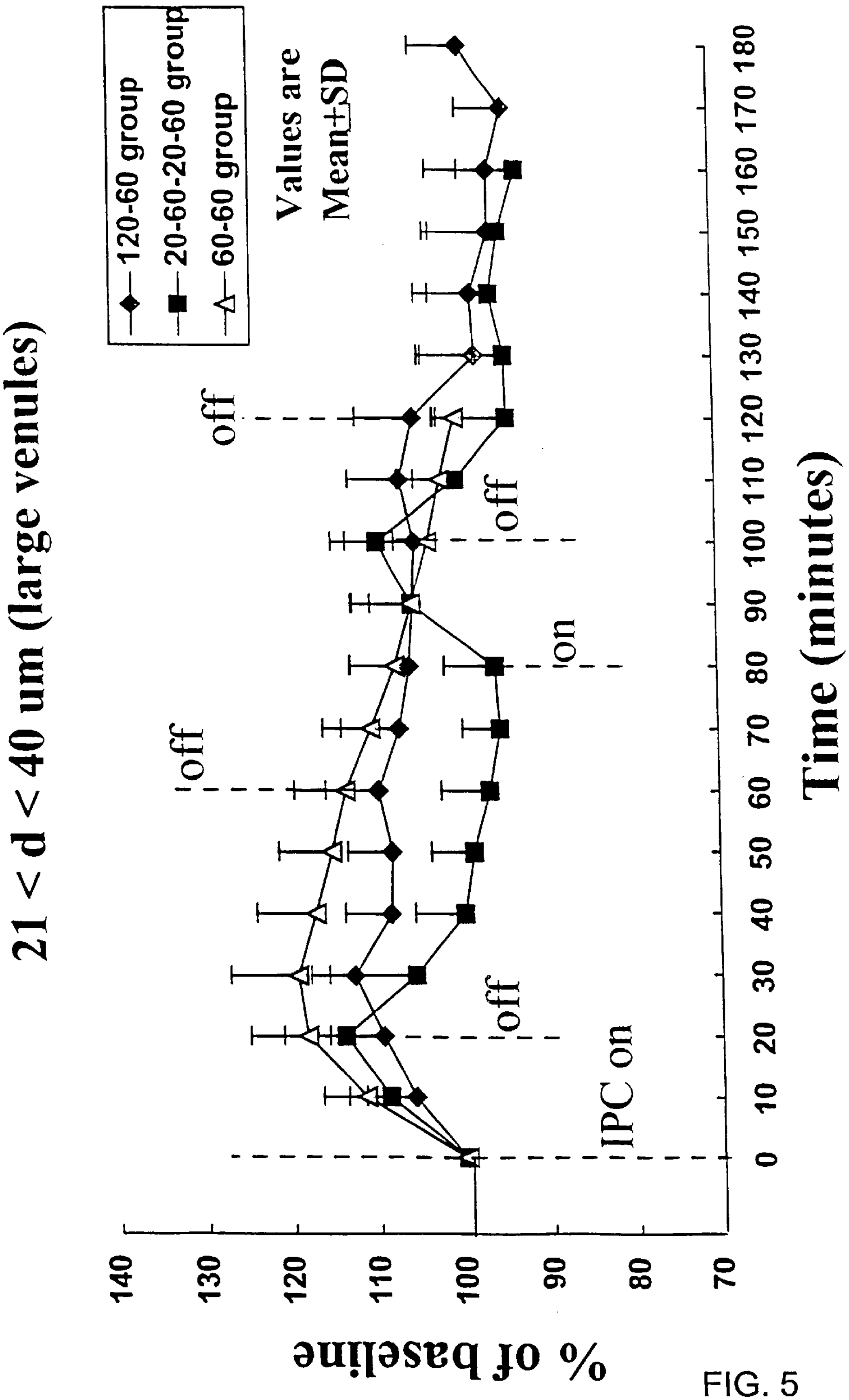
FIG. 5 is a graph showing vasodilation of large venules in the cremaster muscle of the same three groups of rats as were tested in FIG. 4.
Figure 6:
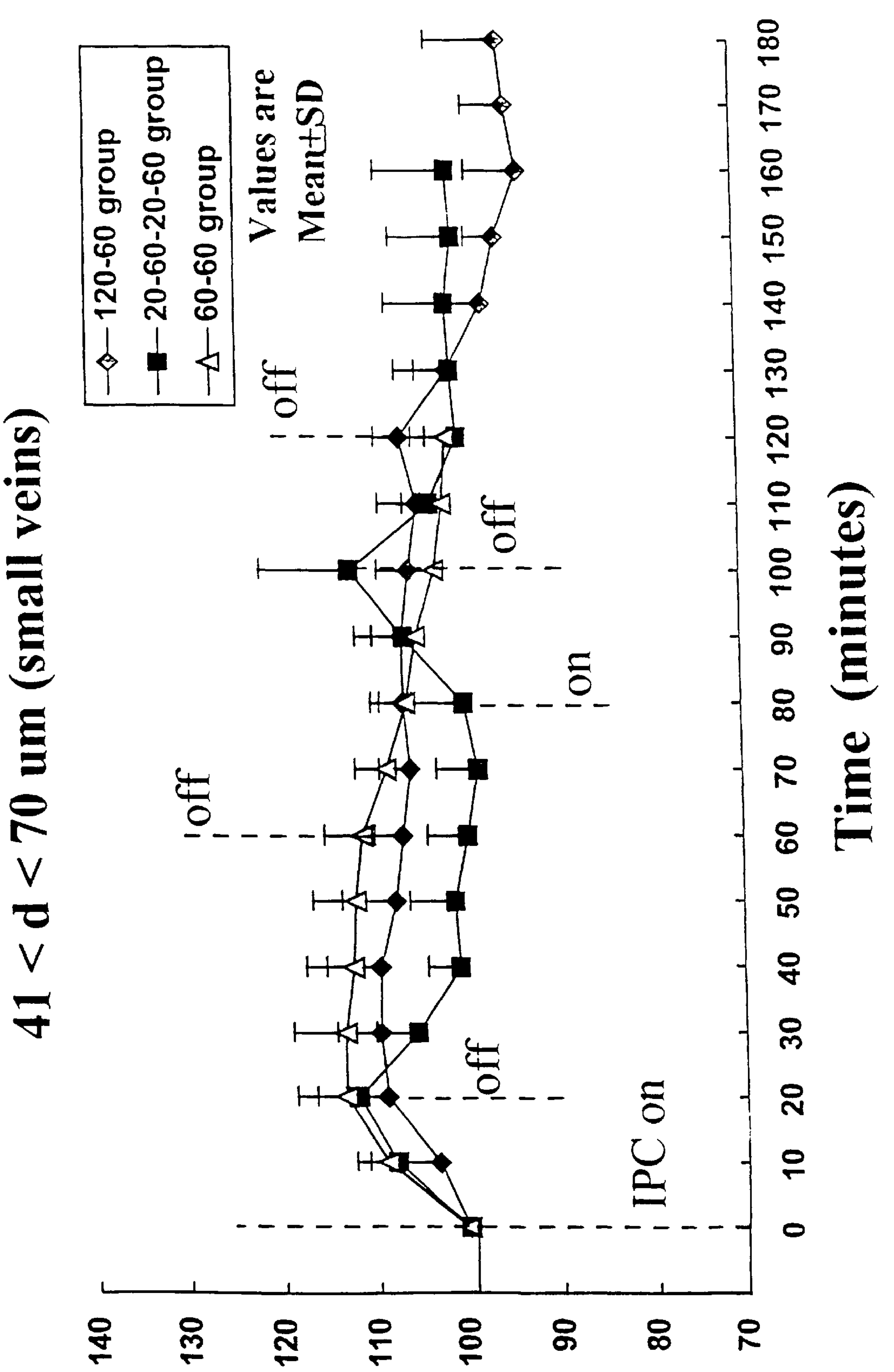
FIG. 6 is a graph showing vasodilation of large veins in the cremaster muscle of the same three groups of rats as were tested in FIGS. 4 and 5.

FIGS. 4, 5, and 6 illustrate the effects in the small venules (10 microns<d<20 microns), the large venules (21 microns<d<40 microns), and the small veins (41 microns<d<70 microns), respectively, of three groups of rats subjected to IPC applied to a hind leg in accordance with the method of the instant invention. The first group was subjected to 120 minutes of IPC followed by 60 minutes of recovery (a 120-60 cycle); the second group was subjected to 20 minutes of IPC, 60 minutes of recovery, another 20 minutes of IPC, and another 60 minutes of recovery (a 20-60-20-60 cycle); and the third group was subjected to 60 minutes of IPC followed by 60 minutes of recovery (a 60-60 cycle). After the IPC application cycle was complete, the vasodilation of vessels in the rat cremaster muscle was measured by videomicroscopy relative to a previously determined baseline, and the percent change values were averaged within each group.

Comparison of data in each of FIGS. 1–6 indicates that application of IPC in accordance with the method of the instant invention can cause corresponding vasodilation in both arterial and venous vessels, and to a level of increased vessel diameter comparable to that achieved with the first application of IPC. It is also observed that IPC-induced vasodilation of both arterial and venous vessels disappears soon after the IPC is stopped. For arterial vessels, vessel diameter can return to the baseline levels as quickly as five minutes. Further, the increase in vessel diameter appears to be dependent entirely on the application of IPC; thus, the increase stops as soon as the IPC is turned off. Finally, comparison of the 40-5-40 and 40-10-40 groups indicates that, at least for the arterial vessels, the duration of the recovery period at either 5 minutes or 10 minutes does not affect the level of vasodilation achieved during the second application of IPC.

The method of the instant invention, whether to be used for enhancement of circulation, venous return, or microcirculation, can be carried out with any commercially available device for IPC, by simply removing the device during the desired recovery periods. Preferably, the inventive method is carried out using a device sold by the assignee Aircast, Inc. of Summit, N.J. under the trademark VENA-FLOW®. In a most preferred embodiment, a VENA-FLOW® intermittent pneumatic compression device is programmed to provide desired pressure, inflation rate, pressure duration, and pulse frequency, and also to provide desired IPC application periods and recovery periods in which lesser or no IPC is applied.

Thus, a method has been disclosed for providing enhanced circulation, venous return and microcirculation by applying IPC in alternating application and recovery periods. Enhanced microcirculation can be observed in skeletal muscle distant from the actual site of IPC application. The inventive method may also provided greater DVT prophylaxis. The recovery periods can be either longer or shorter than the IPC application periods. The recovery periods can be defined by the complete absence of IPC, or the application of IPC at lower pressures, pulse rises, or pulse frequency. During the application periods, the IPC can be applied at predetermined pressures, pulse rises, and pulse frequencies. Other operations parameters will be readily apparent to those skilled in the art.

The invention has been shown and described herein by way of illustration and not by way of limitation. The inventor envisions, and it will be apparent to those skilled in the art, that other variations and modifications of the embodiment described herein are all within the intended scope and spirit of the invention. Accordingly, the patent is not to be limited in scope and effect to any specific embodiment described nor in any other way that is inconsistent with the extent to which the progress and the art has been advanced by the invention.

I claim:

1. A method for providing enhanced circulation in a body portion of a subject, the method comprising a) providing a means for applying intermittent pneumatic compression to a limb of a subject's body, said intermittent pneumatic compression comprising a sequence of alternating pressurization and depressurization of said limb, and b) applying intermittent pneumatic compression to the limb in a pre-determined pattern, said pattern comprising a first period of application of intermittent pneumatic compression, a period of recovery, and a second period of application of intermittent pneumatic application; said period of recovery being characterized by one or more of i) absence of intermittent pneumatic compression, ii) application of intermittent pneumatic compression at a lower pressure, iii) application of intermittent pneumatic compression at a lower pulse rise, and iv) application of intermittent pneumatic compression at a lower pulse frequency.

2. The method of claim 1 wherein said pre-determined pattern comprises a period of recovery that is of shorter duration than said first period of application of intermittent pneumatic compression.

3. The method of claim 2 wherein said pre-determined pattern comprises a first period of intermittent pneumatic compression application of about 40 minutes and a recovery period of about 5 minutes.

4. The method of claim 2 wherein said pre-determined pattern comprises a first period of intermittent pneumatic compression application of about 40 minutes and a recovery period of about 10 minutes.

5. The method of claim 2 wherein said pre-determined pattern comprises a first period of intermittent pneumatic compression application of about 120 minutes and a recovery period of about 60 minutes.

6. The method of claim 1 wherein said pre-determined pattern comprises a period of recovery that is of longer duration than said first period of application of intermittent pneumatic compression.

7. The method of claim 6 wherein said pre-determined pattern comprises a first period of application at intermittent pneumatic compression of about 20 minutes and a recovery period of about 60 minutes.

8. The method of claim 1 wherein said predetermined pattern comprises a period of recovery that is of about equal duration to the first period of application of intermittent pneumatic compression.

9. The method of claim 8 wherein said pre-determined pattern comprises a first period of application of intermittent pneumatic compression of about 60 minutes and a recovery period of about 60 minutes.

* * * * *